(12) United States Patent
Johnson et al.

(10) Patent No.: US 9,101,505 B2
(45) Date of Patent: Aug. 11, 2015

(54) COMPOSITE STENT

(75) Inventors: James R. Johnson, Stillwater, MN (US); Anita Tavakley, Burnsville, MN (US)

(73) Assignee: BRS Holdings, LLC, Rosemount, MN (US)

(*) Notice: Subject to any disclaimer, the term of this patent is extended or adjusted under 35 U.S.C. 154(b) by 1406 days.

(21) Appl. No.: 11/932,531

(22) Filed: Oct. 31, 2007

(65) Prior Publication Data

US 2008/0077222 A1    Mar. 27, 2008

Related U.S. Application Data

(63) Continuation-in-part of application No. 11/380,572, filed on Apr. 27, 2006.

(51) Int. Cl.
| | |
|---|---|
| A61F 2/92 | (2013.01) |
| A61L 31/00 | (2006.01) |
| A61L 31/10 | (2006.01) |
| A61L 31/12 | (2006.01) |
| A61L 31/14 | (2006.01) |
| A61F 2/82 | (2013.01) |

(52) U.S. Cl.
CPC ................. *A61F 2/92* (2013.01); *A61L 31/005* (2013.01); *A61L 31/10* (2013.01); *A61L 31/127* (2013.01); *A61L 31/148* (2013.01); *A61F 2/82* (2013.01); *A61F 2210/0076* (2013.01); *A61F 2230/0091* (2013.01)

(58) Field of Classification Search
USPC ........... 623/1.13, 1.39, 1.41, 1.44, 1.46, 1.49, 623/23.56, 23.7; 606/77, 154, 908
See application file for complete search history.

(56) References Cited

U.S. PATENT DOCUMENTS

| | | | |
|---|---|---|---|
| 3,436,307 A | | 4/1969 | Johnson et al. |
| 3,444,929 A | | 5/1969 | Brown et al. |
| 3,709,706 A | | 1/1973 | Sowman |
| RE27,747 E | | 9/1973 | Johnson |
| 3,795,524 A | | 3/1974 | Sowman |
| 4,166,147 A | | 8/1979 | Lange et al. |
| 4,649,920 A | | 3/1987 | Rhum |
| 4,655,777 A | * | 4/1987 | Dunn et al. .................... 424/423 |
| 4,801,562 A | | 1/1989 | Sowman et al. |
| 5,084,051 A | | 1/1992 | Tormala et al. |
| 5,629,077 A | | 5/1997 | Turnlund et al. |

(Continued)

FOREIGN PATENT DOCUMENTS

| | | |
|---|---|---|
| EP | 1 639 962 A2 | 12/2000 |
| EP | 1 721 625 A2 | 2/2006 |

(Continued)

OTHER PUBLICATIONS

Alumina-reinforced polymer has high strength, flexibility, *Advanced Materials & Processes*, May 2008, p. 17 (1 page).

(Continued)

*Primary Examiner* — Brian Pellegrino
(74) *Attorney, Agent, or Firm* — Brian E. Szymanski

(57) ABSTRACT

A bioremovable composite stent includes bioremovable polymer and bioremovable ceramic flakes generally coupled with adjacent layers of bioremovable polymer so as to make a resilient composite stent configured to move between a contracted configuration to an expanded configuration. In one embodiment, the composite stent may have a helical shape.

23 Claims, 5 Drawing Sheets

(56) References Cited

U.S. PATENT DOCUMENTS

| | | | |
|---|---|---|---|
| 5,728,150 | A | 3/1998 | McDonald et al. |
| 5,980,564 | A | 11/1999 | Stinson |
| 6,136,029 | A | 10/2000 | Johnson et al. |
| 6,221,075 | B1 * | 4/2001 | Tormala et al. ............... 606/77 |
| 6,296,667 | B1 | 10/2001 | Johnson et al. |
| 6,325,822 | B1 | 12/2001 | Chouinard et al. |
| 6,338,739 | B1 | 1/2002 | Datta et al. |
| 6,368,703 | B1 | 4/2002 | Johnson |
| 6,409,750 | B1 | 6/2002 | Hyodoh et al. |
| 6,527,810 | B2 | 3/2003 | Johnson et al. |
| RE38,158 | E | 6/2003 | Barrows et al. |
| 6,605,648 | B1 | 8/2003 | Johnson et al. |
| 6,623,521 | B2 | 9/2003 | Steinke et al. |
| 6,626,936 | B2 | 9/2003 | Stinson |
| 6,641,609 | B2 | 11/2003 | Globerman |
| 6,652,575 | B2 | 11/2003 | Wang |
| 6,656,218 | B1 | 12/2003 | Denardo et al. |
| 6,656,587 | B2 | 12/2003 | Johnson et al. |
| 6,719,934 | B2 | 4/2004 | Stinson |
| 6,747,121 | B2 | 6/2004 | Gogolewski |
| 6,749,629 | B1 | 6/2004 | Hong et al. |
| 6,805,705 | B2 | 10/2004 | Hong et al. |
| 6,814,750 | B2 | 11/2004 | Kavteladze et al. |
| 6,849,186 | B2 | 2/2005 | Johnson et al. |
| 6,854,172 | B2 | 2/2005 | Kaese et al. |
| 6,869,445 | B1 | 3/2005 | Johnson |
| 6,890,350 | B1 | 5/2005 | Walak |
| 6,913,619 | B2 | 7/2005 | Brown et al. |
| 6,913,762 | B2 | 7/2005 | Caplice et al. |
| 6,929,626 | B2 | 8/2005 | DiCarlo et al. |
| 6,972,130 | B1 | 12/2005 | Lee et al. |
| 6,977,095 | B1 | 12/2005 | Marx et al. |
| 6,984,671 | B2 | 1/2006 | Johnson et al. |
| 6,991,647 | B2 | 1/2006 | Jadhav |
| 6,993,406 | B1 | 1/2006 | Cesarano, III et al. |
| 6,997,948 | B2 | 2/2006 | Stinson |
| 7,108,716 | B2 | 9/2006 | Burnside et al. |
| 2002/0077693 | A1 * | 6/2002 | Barclay et al. ............... 623/1.13 |
| 2002/0103527 | A1 | 8/2002 | Kocur et al. |
| 2003/0125739 | A1 * | 7/2003 | Bagga et al. ................. 606/61 |
| 2004/0054413 | A1 * | 3/2004 | Higham et al. ............ 623/17.16 |
| 2004/0152034 | A1 * | 8/2004 | Cummings et al. ............... 433/8 |
| 2005/0163821 | A1 | 7/2005 | Sung |
| 2005/0163954 | A1 | 7/2005 | Shaw |
| 2005/0239628 | A1 | 10/2005 | Johnson et al. |
| 2006/0045901 | A1 | 3/2006 | Weber |
| 2006/0199876 | A1 | 9/2006 | Troczynski et al. |
| 2006/0264531 | A1 | 11/2006 | Zhao |
| 2007/0207186 | A1 | 9/2007 | Scanlon et al. |

FOREIGN PATENT DOCUMENTS

| | | |
|---|---|---|
| EP | 1 634 609 A2 | 3/2006 |
| WO | WO 9818408 A1 | 5/1998 |
| WO | WO 02/060337 A2 | 8/2002 |
| WO | WO 03/068288 A1 | 8/2003 |
| WO | WO 2004/024201 A2 | 3/2004 |
| WO | WO 2006/014969 A2 | 2/2006 |

OTHER PUBLICATIONS

International Search Report and Written Opinion, obtained from corresponding International Application No. PCT/US2008/082114, May 19, 2009 (16 pgs.).

Invitation to Pay Additional Fees and Communication Relating to the Results of the Partial International Search, obtained from related International Patent Application No. PCT/US2008/082114, Mar. 6, 2009 (6 pages).

Information on Related Patents and Patent Applications, see the section of the accompanying Information Disclosure Statement Letter entitled "Related Patents and Patent Application" for further information, Jul. 19, 2007.

"Implantable Elution Devices: Reshaping the Industry," devicelink.com/mddi, MD & DI, Jul. 2005, pp. 54-55 (2 pages).

Kling, Jim, "Elution, Boston Scientific's blockbuster medical device—and the novel way it was developed," printed from webstie www.technologyreivew.com on Apr. 27, 2006 (3 pages).

"MIV Therapeutics' Hap Nano Stent Coating Demonstrates Excellent Biocompatibility," Archived Nanotechnology News, Posted Mar. 10, 2005 (2 pages).

Smock, Doug, "Medial Miracles," Design News, Aug. 15, 2005, vol. 7 (9 pages).

Information on Related Patents and Patent Applications, see the section of the accompanying Information Disclosure Statement Letter entitled "Related Patents and Patent Applications" for further information, Jul. 19, 2007.

International Search Report and Written Opinion, PCT Application No. PCT/US07/67546, Nov. 8, 2007 (17 pages).

Di Mario, Carlo, M.D., et al., Drug-Eluting Bioabsorbable Magnesium Stent, *Journal of Interventional Cardiology*, vol. 17, No. 6, 2004, pp. 391-395 (5 pages).

Eberhart, Robert C., et al., Bioresorbable Polymeric Stents: Current Status and Future Promise, *J. Biomater: Sci. Polymer Edn.* vol. 14, No. 4, 2003, pp. 299-312 (14 pages).

Singh, J. P. et al. YBa2Cu3O(x) composites with improved toughness and strength. SAO/NASA ADS Physics Abstract Service. Apr. 1990. (Abstract only).

S. Newman and F. J. Meyer, Mica Composites of Improved Strength. Polymer Composites, Sep. 1980, vol. 1, No. 1.

* cited by examiner

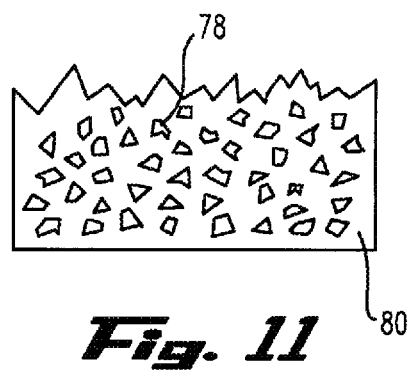
Fig. 10
Fig. 11
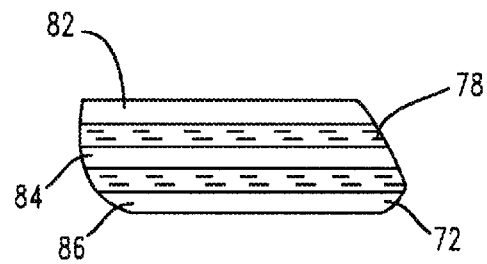
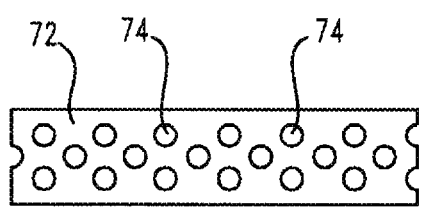
Fig. 12
Fig. 13
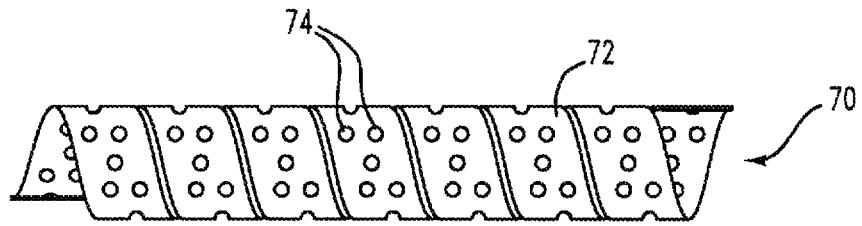
Fig. 14
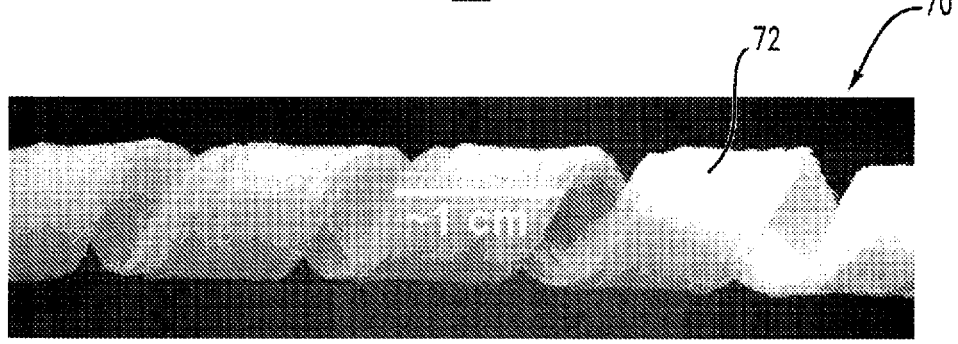
Fig. 15

COMPOSITE STENT

CROSS-REFERENCE TO RELATED PATENT APPLICATIONS

This patent application is a continuation-in-part of U.S. patent application Ser. No. 11/380,572, entitled "Composite Stent," filed on 27 Apr. 2006, which is hereby incorporated herein by reference in its entirety. In the event of a conflict, the subject matter explicitly recited or shown herein controls over any subject matter incorporated by reference. All definitions of a term (express or implied) contained in any of the subject matter incorporated by reference herein are hereby disclaimed. The paragraphs shortly before the claims dictate the meaning to be given to any term explicitly recited herein subject to the disclaimer in the preceding sentence.

BACKGROUND

Blood vessels, the esophagus, intestines, endocrine gland ducts, the urethra and other lumens are all subject to strictures i.e., a narrowing or occlusion of the lumen. Strictures can be caused by a variety of traumatic or organic disorders and symptoms can range from mild irritation and discomfort to paralysis and death.

Most life threatening stenoses are associated with the cardiovascular system and are often treated by performing a percutaneous coronary intervention (PCI) such as balloon angioplasty (also referred to as percutaneous transluminal coronary angioplasty or PTCA). Balloon angioplasty is performed by threading a slender balloon-tipped catheter from an artery in the groin to a trouble spot in an artery of the heart. Once in position, the balloon is inflated to thereby dilate (widen) the narrowed coronary artery so that blood can flow more easily. Unfortunately, experience has shown that three to six months after PCI, many patients experience restenosis (some estimates place the number at between a third and half of all patients experience restenosis). Injury to the arterial wall during PCI is believed to be the initiating event that causes restenosis. The resulting stricture is often formed from vascular smooth muscle cell proliferation and extracellular matrix secretion at the injured site. Restenosis is also a major problem in non-coronary artery disease including the carotid, femoral, iliac, popliteal and renal arteries.

Other non-vascular tubular structures can also suffer from stenosis due to a variety of causes such as inflammation, neoplasm, and benign intimal hyperplasia. Some strictures such as those in the esophagus or intestines, may be surgically removed and the lumen repaired by anastomosis. The smaller transluminal spaces associated with ducts and vessels may also be repaired in this fashion. Unfortunately, restenosis caused by intimal hyperplasia is common in these situations.

Aging men often suffer from stenosis of the urethra that results in diminished urine flow rates. The most frequent cause is enlargement of the prostate gland (e.g., benign prostatic hypertrophy or BPH). In this disease, the internal lobes of the prostate slowly enlarge and progressively occlude the urethral lumen. A number of therapeutic options are available for treating an enlarged prostate. These include watchful waiting (no treatment), several drugs, a variety of so-called "less invasive" therapies, and transurethral resection of the prostate (TURP)—long considered the gold standard.

In the urethra, a circumferential band of fibrous scar tissue may progressively contract and narrow the lumen thereby reducing the urine flow rate. A stricture of this type may be congenital or may result from urethral trauma or disease. These strictures were traditionally treated by dilation with sounds or bougies. More recently, balloon catheters have been used to mechanically dilate the lumen. Surgical urethrotomy is currently the preferred treatment, but restenosis remains a significant problem.

Stents were developed, at least in part, to attempt to minimize the occurrence of restenosis. Stents can generally be thought of as a form of mechanical scaffolding that holds the occluded lumen open. There are two general types of stents: permanent and temporary. Temporary stents can be further subdivided into removable and absorbable.

Permanent stents are used where long term structural support or restenosis prevention is required, or in cases where surgical removal of the implanted stent is impractical. Permanent stents are usually made from metals such as Phynox, 316 stainless steel, MP35N alloy, and superelastic Nitinol (nickel-titanium).

Although stents are used primarily in the vasculature, stents may also be used to hold any bodily lumen open. For example, stents may be used as temporary devices to prevent closure of a recently opened urethra following minimally invasive procedures to treat an occlusion due to an enlarged prostate. These procedures often result in a post treatment edema and urethral obstruction. In these cases, the stent is typically not covered with tissue (epithelialized) prior to removal.

Temporary absorbable stents can be made from a wide range of synthetic biocompatible polymers depending on the physical qualities desired. Representative biocompatible polymers include polyanhydrides, polycaprolactone, polyglycolides, polylactides, and polyphosphate esters.

Recently, a number of biocompatible, bioresorbable materials have been used in stent development and in situ drug delivery development. These stents are designed and made from copolymers which unfortunately may not provide the desired physical properties required to hold the lumen open for a sufficient time period for healing to occur. Accordingly, it would be desirable to provide an improved biocompatible, bioresorbable stent that has the desired physical properties necessary to hold the lumen open for a time sufficient to promote healing. Also, it would be desirable to provide a stent that has a substrate that facilitates the growth or regeneration of tissue as the substrate is removed by or incorporated into the patient's body.

SUMMARY

Various embodiments of a composite stent are described herein. The composite stent is used to support and/or dilate an occluded bodily lumen or vessel. The composite stent may be sized and/or otherwise configured to support and/or dilate any tubular passages in the body such as blood vessels, urethra, intestines, endocrine gland ducts, esophagus, and so forth. The composite stent is configured to move between a contracted configuration where the composite stent is sized to be inserted into and transported through the bodily lumen and an expanded configuration where the composite stent is sized to support and/or dilate the bodily lumen.

The composite stent is bioremovable. After the composite stent is implanted, it slowly degrades. The composite stent is designed to degrade at a rate that keeps the stent in place long enough to allow the lumen to remain open without the assistance of the composite stent. Due to its bioremovability, the composite stent reduces long-term complications associated with permanent stents and/or eliminates the need to surgically remove the stent at a later time. The degradation rate of the composite stent can be altered by changing the composition of the materials that are used to make the composite stent. The composite stent may also degrade in a way that prevents chunks from spalling off of the stent and causing clots or other blockages. In one embodiment, the composite stent includes bioremovable polymer and bioremovable ceramic material. The bioremovable ceramic material may be provided as a plurality of fibers or flakes. Preferably, the bioremovable polymer includes polylactide, polyglycolide, and/or polycaprolactone and the bioremovable ceramic material includes calcium phosphate material such as tricalcium phosphate.

It should be appreciated that the term "bioremovable" is used herein to refer to biocompatible materials that are capable of being broken down, gradually absorbed, and/or otherwise used by or eliminated from the body by processes such as bioabsorbtion (i.e., they are absorbed by the body and moved within the body to be used), biodegradation (i.e., chemically fall apart into non-toxic components that are carried away by material moving through the lumen), and the like. Thus, the term "bioremovable" is intended to encompass both bioabsorbtion and biodegradation processes.

The inclusion of the bioremovable ceramic material provides a number of advantages to the composite stent. For example, the inclusion of flakes or fibers of bioremovable ceramic material provides additional stiffness and/or strength to the composite stent. The increased strength may prevent the composite stent from being compressed or otherwise deformed by the force of the walls of the lumen pressing against it. The bioremovable ceramic material may also function as a source of calcium (e.g., bioremovable ceramic material includes tricalcium phosphate) to facilitate tissue regeneration and/or repair. In some embodiments, the bioremovable ceramic material may be porous. The pores may provide a number of advantages such as providing a substrate structure that promotes rapid cell growth to occur. The pores may also be loaded with a bioactive agent such as drugs, stem cells, and the like. As the composite stent slowly degrades and exposes the bioremovable ceramic material, the bioactive agents may be slowly released to provide a therapeutic effect.

It should be appreciated that the composite stent may have any of a number of suitable configurations. In one embodiment, the composite stent may include a loose network of fibrous material that is configured to expand in a bodily lumen. The fibrous material may include a plurality of composite yarns that are woven together. The composite yarns may include a core of bioremovable ceramic fibers encased in one or more coatings of bioremovable polymers. The outer coating of bioremovable polymer may be selected to provide a slightly tacky surface. As the composite stent is expanded in the bodily lumen, the surface forces between the bioremovable polymer coatings on adjacent yarns holds the composite stent in an expanded position.

In another embodiment, the composite stent may include a plurality of layers of different materials. For example, the composite stent may include two or more layers that have different physical properties and/or compositions. The composite stent may include alternating layers of bioremovable polymer that have a high concentration of bioremovable ceramic material and a low concentration of bioremovable ceramic material. The high concentration layers may include bioremovable ceramic material dispersed or embedded in bioremovable polymer. The low concentration layers may include very small amounts of bioremovable ceramic material or may be completely free of bioremovable ceramic material.

In one embodiment, the composite stent may include a plurality of flakes of bioremovable ceramic material. The flakes may be dispersed or embedded in bioremovable polymer. In one embodiment, the flakes may be embedded in a layer of bioremovable polymer so that the flakes are approximately parallel to each other and/or the surface of the layer. Orienting the flakes in parallel acts to enhance the physical properties of the composite stent such as elastic modulus, strength, resiliency, and so forth. The flakes strengthen the layer of bioremovable composite material along both the width and length of the layer. Chopped fibers of bioremovable ceramic material may also be embedded or dispersed in the composite stent. In one embodiment, the chopped fibers may be oriented parallel to each other. For example, the chopped fibers may be oriented parallel to a lengthwise direction of the layer. In this configuration, the chopped fibers increase the stiffness of the layer in a lengthwise direction, but may not provide any increase or may provide a small increase in the stiffness in the crosswise direction.

The composite stent has a shape that allows it to move between a contracted configuration where the composite stent is sized to be inserted into the lumen of the patient and an expanded configuration where the composite stent is sized to support and/or dilate the lumen. In one embodiment, the composite stent may have a helical shape. The composite material used to make the composite stent may be resilient in nature. The resilient properties of the composite material may cause the composite stent to move from the contracted configuration where the composite stent is wound and in a state of tension to the expanded configuration where the composite stent is substantially unwound. It should be appreciated that when the composite stent is deployed in the lumen, the composite stent is not fully at a state of rest, but is still under enough tension to hold the composite stent in place and to support and/or dilate the lumen. In another embodiment, the composite stent may take the form of a coiled sheet that can be expanded radially in the lumen.

The bioremovable composite material used to make many of the embodiments of the composite stent can be prepared using any suitable process. In one embodiment, the different layers of material may be prepared individually and coupled together to form the layered bioremovable composite material. For example the different layers of bioremovable polymer having high and low concentrations of bioremovable ceramic material may be extruded or molded individually. The individual layers may be coupled together by heating a sandwich of layers or slightly solvating the surface of each layer before applying the next layer. In the extrusion process, the high concentration layers may be made by extruding a mixture of bioremovable polymer and bioremovable ceramic material into a ribbon or strip of bioremovable composite material. The low concentration layers may be made by extruding bioremovable polymer into a ribbon. In the cast and mold process, ribbons of bioremovable polymer and ribbons of a combination of bioremovable polymer and bioremovable ceramic material may be made by casting the liquid bioremovable polymer and the mixture of bioremovable polymer and bioremovable ceramic material into molds. Once the ribbons have dried, the ribbons may be removed from the mold and coupled together to form a layered bioremovable composite material. The bioremovable composite material made using either process can then be used to make the finished composite stent.

In another embodiment, the bioremovable composite material may be prepared by extruding a mixture of bioremovable polymer and bioremovable ceramic material in the shape of a tube. The tube may be cut to have a resilient helical shape as described above. The bioremovable composite material may also be prepared using an integrated process where the different layers of material are simultaneously extruded and immediately coupled together.

The foregoing and other features, utilities, and advantages of the subject matter described herein will be apparent from the following more particular description of certain embodiments as illustrated in the accompanying drawings.

DRAWINGS

FIGS. 10 and 11 show a side view and a top view of another embodiment of a composite material that may be used to make another embodiment of the composite stent. The ceramic material is depicted as being oriented roughly parallel to the top surface of the composite material.

FIG. 12 shows a side view of another embodiment of a layered composite material that may be used to make another embodiment of the composite stent.

FIGS. 13 and 14 show a top view of a ribbon of composite material (FIG. 13) that may be wound into a helical shape to make another embodiment of a composite stent (FIG. 14).

FIG. 15 is a photograph of another embodiment of a composite stent having a helical shape.

DETAILED DESCRIPTION

Although the subject matter described herein is provided in the context of stents generally, it should be appreciated that certain embodiments may be more suitable for a particular application than other embodiments. For example the stent shown in FIG. 1 may be more suited for intravascular use than for use in other lumens. Also, the stent shown in FIG. 5 may be more suited for use in the intestines or in other relatively larger lumens. That being said, it should be appreciated that any of the stents described herein may be configured to be used in any suitable lumen in the body. Also, it should be appreciated, that the features, advantages, characteristics, etc. of one embodiment may be applied to any other embodiment to form an additional embodiment unless noted otherwise.

Figure 1:
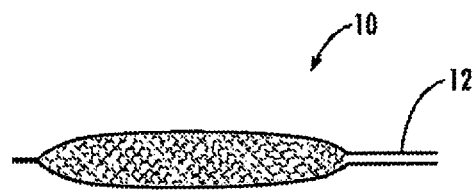
FIG. 1 shows a side view of a composite stent in a contracted configuration to allow the stent to be inserted into a lumen.

Embodiments of Composite Stents that Use Fibrous Bioremovable Composite Material Referring to FIG. 1, a composite stent 10 is shown in a contracted configuration or first configuration where the diameter or size of the stent 10 is reduced to allow the stent 10 to be inserted into a lumen or vessel. The stent 10 is formed from a loose woven network of fibrous composite material. The stent 10 has a generally cylindrical or tubular shape that is configured to fit within a lumen. The stent 10 is bioremovable to allow the stent 10 to be safely and effectively removed over time from the lumen.

Figure 2:
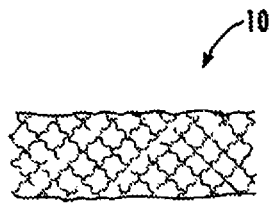
FIG. 2 shows a side view of the composite stent of FIG. 1 in an expanded configuration to hold a lumen open.

In order to facilitate insertion into the lumen, the stent 10 may be releasably coupled to a catheter or guide wire 12. The catheter 12 is configured to allow the catheter 12 and stent 10 to pass through the lumen to the occluded site. Once the stent 10 is in position, the stent 10 can be expanded to open the occluded lumen and hold it open. In one embodiment, as the stent 10 is expanded, it may become shorter in length and larger in diameter as illustrated in FIG. 2. The catheter 12 may then be withdrawn from the lumen leaving the stent 10 in place.

It should be noted that for purposes of this disclosure, the term "coupled" means the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature.

It should be appreciated that numerous methods may be used to expand the stent 10. In one embodiment, the catheter 12 may be a balloon catheter having a balloon positioned between the stent 10 and the main body of the catheter 12. The balloon can be inflated using a fluid such as saline solution. As the balloon is inflated, the stent 10 expands outward radially until the stent 10 is positioned to hold the lumen open. In general, the stent 10 is configured to expand in a lumen without substantial rotational movement relative to the longitudinal axis of the stent 10 (see stent 30 for an example where the stent expands by rotating about the longitudinal axis of the stent 30).

Figure 3:
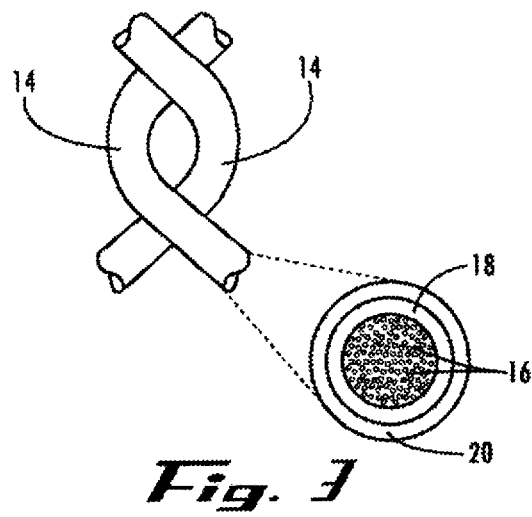
FIG. 3 shows a perspective and cross-sectional view of one embodiment of a composite yarn or fiber that may be used to form at least a part of the composite stent of FIG. 1.

It should be appreciated that any suitable bioremovable fibrous material may be used to form the stent 10 (e.g., inorganic fibrous material). Referring to FIG. 3, the fibrous material may include a loose network of composite yarns or composite fibers 14. The composite yarns 14 may be woven together in a loose weave such as that shown in FIG. 3, or the composite yarns 14 may be assembled in other ways besides weaving (e.g., using a suitable rubbery biodegradable polymer to engage the fibers to resist the movement of the fibers so as to enhance the structural integrity of the composite). It should be appreciated that the composite yarns 14 may be assembled together in a manner that allows the composite yarns 14 to expand so that the stent 10 can likewise expand to fill the lumen. At the same time, the composite yarns 14 should be configured so that upon expansion of the stent 10, the stent 10 has sufficient strength to remain in position in the lumen and keep the occluded site open.

FIG. 3 also shows a cross-sectional view of one of the composite yarns 14. Each composite yarn 14 includes a plurality of ceramic fibers 16 encased in or coated with a first or inner polymer layer or coating 18 which is in turn coated with a second or outer polymer layer or coating 20. It should be appreciated that the ceramic fibers 16 may be soaked with the first polymer coating 18 to completely fill in the interstices between the ceramic fibers 16, or the ceramic fibers 16 may be individually coated with the first polymer coating 18. The first polymer coating 18 may be provided to give resiliency and toughness to the composite yarn 14 by distributing the load on the ceramic fibers. The second polymer coating 20, a more rubbery bioremovable polymer than the first polymer coating 18, may engage the fibers 16/yarn 14 to make firm the structural integrity of the expanded stent 10. Thus, the first polymer coating 18 may have a different modulus of elasticity than the second polymer coating 20. In one embodiment, the first polymer coating 18 has a higher modulus of elasticity than the second polymer coating 20. Also, the first polymer coating 18 may have a different molecular weight than the second polymer coating 20. In one embodiment, the first polymer coating 18 may have a lower molecular weight than the second polymer coating 20.

The higher friction property of the second polymer coating 20 holds the composite yarns 14 in the expanded state by friction forces and prevents the stent 10 from collapsing. It should be appreciated that the composite yarns 14 may include more than one polymer coating 18, 20. For example, the composite yarns 14 may be prepared by forming multiple resilient coatings over the ceramic fibers 16 with the final coating being a low modulus coating. The thickness of the first polymer coating 18 and the second polymer coating 20 may be about 0.1 to 5 microns.

It should be appreciated that in other embodiments of the stent 10 a single polymer coating may be used or more than one polymer coating (e.g., three or more) may be used. For example, a single polymer coating may suffice so long as the polymer coating has the requisite stiffness to support the integrity of the stent 10 and the friction properties sufficient to hold the stent 10 in the expanded position. Also, bodily fluids (e.g., blood, etc.) may soften the surface of the polymer so that the polymer provides sufficient friction to hold the stent 10 open.

The stent 10 may be configured to gradually and uniformly erode in the lumen (e.g., in the bloodstream of a patient) rather than erode by periodically cleaving off large chunks. In one embodiment, each layer may be selected to provide protection against nonuniform erosion of the layer beneath it. The materials used in the stent 10 may be selected to provide sufficient support for the lumen at all times as the stent 10 is replaced by natural tissues.

The first polymer coating 18 and the second polymer coating 20 for the stent 10 may include biocompatible, bioremovable polymers. That is, the polymers will be removed by in-vivo processes such that the polymers and their products are not toxic or inhibit the purpose of the stent 10 and the products will be either eliminated from the body or assimilated by the body. Suitable examples of such polymers may be found among polyesters, polyols, polycarbonates, polyamides, polyethers, polysaccharides, and/or polyhydroxyalkanoates. Preferred examples include polylactides (PLA), polyglycolides (PGA), polycaprolactones (PCL), albumin, collagen, copolymers of any of these polymers, and/or mixtures thereof. PLA is used to refer to poly-L-lactide (PLLA) and/or poly-DL-lactide (PDLLA). In one embodiment, the first polymer coating 18 and the second polymer coating 20 each includes PLA, PGA, PCL and/or copolymers thereof.

The first polymer coating 18 is intended to provide a protective load-distributing layer on the ceramic fibers to inhibit fracture when the fibers are moved upon expanding the stent 10. It may also have additional advantages such as modulating the rate of bioremoval and providing some inter-surface friction between fibers. The polymer should have sufficient molecular entanglement to provide some toughness as well as the above features.

The second polymer coating 20 is designed to have a glass transition temperature below body temperature. Its function is to further stabilize the open stent from retracting by increased friction, fiber on fiber, yarn on yarn, akin to locking the fibers in place. For example, the second polymer coating 20 may be a bioremovable polymer or copolymer of albumin having a modulus of less than $1 \times 10^7$ pascals. Further it is contemplated that the weave of the yarn that forms the stent 10 may provide some mechanical resistance to retracting when open.

Figure 4:
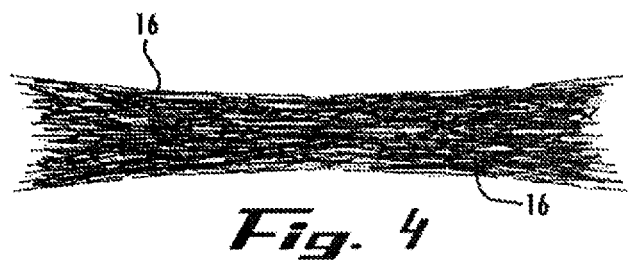
FIG. 4 shows a side view of a plurality of ceramic fibers which may be used in the composite yarn of FIG. 3.

FIG. 4 shows the ceramic fibers 16 prior to being coated with the first polymer coating 18. The ceramic fibers 16 are generally positioned parallel to each other prior to being coated with the first polymer coating 18. The ceramic fibers 16 may be any suitable size. In one embodiment, the ceramic fibers 16 may be about 0.5 microns to 10 microns in diameter or may be about 1 micron to 5 microns in diameter.

The ceramic fibers 16 may be made of any suitable bioremovable ceramic material(s). Suitable examples of bioremovable ceramic material include calcium phosphate material such as tricalcium phosphate and/or other similar materials. Although a number of ceramic materials have been referred to in the literature as "resorbable," many of these compounds, such as hydroxyapatite, are in fact only weakly resorbable. Calcium phosphate compounds such as tricalcium phosphate, on the other hand, are much more resorbable in comparison and are therefore preferred for use in the composite stent. In one embodiment, the tricalcium phosphate is amorphous. It should be noted that calcium phosphate materials are generally bioabsorbed (i.e., incorporated into the body) rather than biodegraded (i.e., removed by the body).

In one embodiment, the bioremovable ceramic material may be substantially entirely made up of tricalcium phosphate. It should be appreciated that in other embodiments, the bioremovable ceramic material may include a mixture of tricalcium phosphate and another bioremovable ceramic material or may be made up entirely of bioremovable ceramic materials other than tricalcium phosphate. In another embodiment, the bioremovable ceramic material may be calcium phosphate material that has been fired to a temperature that makes it strong enough to endure the bending movements which occur during emplacement of the composite stent 10.

Although calcium phosphate materials are preferred for use as the bioremovable ceramic material, other suitable bioremovable ceramic materials may also be used. Additional bioremovable ceramic materials include bioactive glasses such as BIOGLASS as well as other similar materials. Unlike tricalcium phosphate, bioglass typically biodegrades and exits the body. In one embodiment, each composite yarn 14 may include multiple different types of bioremovable ceramic fibers 16. For example, the composite yarn 14 may include a mixture of bioactive glass fibers, tricalcium phosphate fibers, and/or other bioremovable ceramic fibers.

The ceramic fibers 16 may be prepared using any suitable process. One suitable process for preparing tricalcium phosphate fibers (beta tricalcium phosphate) is the sol gel process described in U.S. Pat. Nos. 3,795,524, 4,801,562, 4,929,578, all of which are incorporated by reference herein in their entireties. The process includes mixing a source of calcium such as calcium acetate, calcium citrate, calcium formamide, other organic and inorganic compounds of calcium, with a source of phosphorous such as phosphoric acid, phosphorous pentoxide, and the like, to yield calcium phosphate. The purity of these materials are expected to meet ASTM F1088-04a specifications for implantable products. The salts are made in aqueous solutions and concentrated in a rotovapor device. The viscosity may be increased to about 1000 to 20000 poises by adding glucose, corn syrup, or polyvinyl pyrrolidone (PVP) up to or more than ⅔ of the total volume. Since fibers are being made, the viscous material is drawn through a spinerette. The resulting fibers are fired at varying temperatures depending on the desired porosity of the ceramic material. To form fully dense ceramic material, the fibers 16 are fired at about 1100 to 1200° C. To form nano porous ceramic material, the fibers are fibers 16 are fired at 750 to 850° C.

The composite yarn 14 may have any suitable size depending on the application. The diameter of the composite yarn 14 depends on the number and size of ceramic fibers 16 used in the composite yarn 14. In one embodiment, each composite yarn 14 is about 20 microns to 150 microns in diameter or 50 microns to 100 microns in diameter. The rate at which the bioremovable inorganic ceramic in the stent 10 is bioremoved may be controlled by altering the porosity, thickness, and compositions of the materials being used. The ratio of the amount of the different polymers and/or copolymers (e.g., PLA, PGA, PCL polymers and/or copolymers thereof) used in a particular polymer coating may be altered to change the rate that the polymer coating degrades to meet the requirements for the coating. The ratio of the various polymers and/or copolymers may be determined for each application to provide the desired degradation rate. Also, other biocompatible chemicals such as plasticizers may be used to control the rate of bioremoval.

Figure 5:
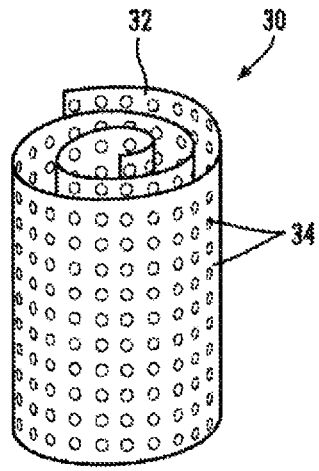
FIG. 5 shows a perspective view of another embodiment of a composite stent in a contracted configuration to allow the stent to be inserted into a lumen.

Embodiments of Composite Stents that Use Sheets or Ribbons of Bioremovable Composite Material Referring to FIG. 5, another embodiment of a composite stent 30 is shown. In this embodiment, the stent 30 includes a sheet 32 having a plurality of holes or openings 34 in it. The stent 30 shown in FIG. 5 is wound or coiled so that it can be inserted into a lumen. Since the stent 30 is not as flexible as the stent 10, the stent 30 may be used in larger lumens such as the intestines or in situations where the stent 30 is implanted directly (often temporarily) into the lumen without passing it through long sections of curved lumen. The stent 30 may be expanded in any suitable manner such as, for example, using a balloon.

Figure 6:
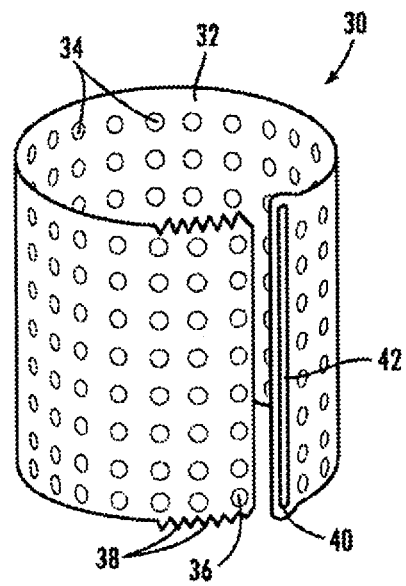
FIG. 6 shows a perspective view of one embodiment of the composite stent from FIG. 5 in an expanded configuration.

As shown in FIG. 6, the stent 30 may be held in the expanded position using a belt and buckle type configuration. The sheet 32 includes a first end 36 which has a plurality of teeth 38 thereon and a second end 40 which includes a buckle shaped opening 42 which is sized to receive the first end 36. When the stent 30 is in the expanded configuration, the teeth 38 engage the top and bottom of the opening 42 to prevent the stent 30 from collapsing. The use of the belt and buckle type configuration allows the stent 30 to be mechanically locked in position. It is also contemplated that the stent 30 may be held open due to the adhesiveness from a low modulus bioremovable polymer coating, for example. The stent 30 may also be held open using a mechanical fastener system such as a slot insert system.

Another embodiment of a composite stent 70 is illustrated in FIG. 14 and shown in a photograph in FIG. 15. The stent 70 includes a ribbon or strip 72 of bioremovable composite material that has a helical shape. In one embodiment, the ribbon 72 may have a plurality of holes 74 in it that expose the interior wall of the lumen as shown in FIG. 14.

The stent 70 may be configured to move from a contracted configuration where the stent 70 is sized to be inserted and moved through the lumen to an expanded configuration where the stent 70 is configured to support and/or dilate the lumen. In one embodiment, the stent 70 may be resilient so that the resilient properties of the stent 70 cause it to move from the contracted configuration to the expanded configuration. For example, the stent 70 may be wound and in a state of tension when the stent 70 is in the contracted configuration. When the stent 70 is wound, the stent 70 becomes longer and the diameter decreases thereby allowing the stent 70 to be inserted into the lumen. A catheter or guidewire may be used to guide the stent 70 to the appropriate location in the lumen while maintaining the stent 70 in the contracted configuration. Once the stent 70 is in place, the tension on the stent 70 may be released (e.g., using a release trigger or other appropriate system on the catheter) to allow the stent 70 to move resiliently to the expanded configuration. In the expanded configuration, the stent 70 contacts the inner surface of the lumen and remains in a state of tension, albeit a lower state of tension than when the stent 70 is in the contracted configuration, to hold the stent 70 in place. The amount of tension that the stent 70 applies to the inner wall of the lumen can be adjusted to meet the patient's requirements (e.g., pediatric uses may require less tension between the stent and the lumen walls).

Figure 7:
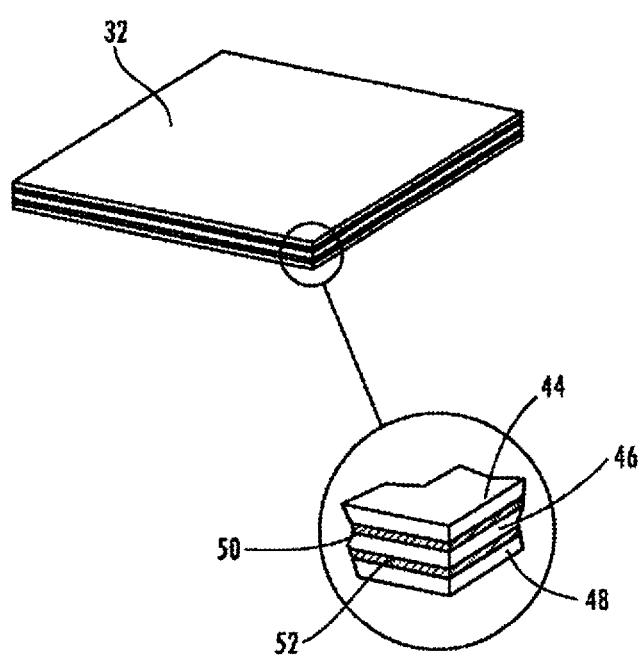
FIG. 7 shows a perspective view of one embodiment of a layered composite material that may be used to form at least part of the composite stent from FIG. 5.

The stents 30, 70 may each include a plurality of layers of different materials as shown in FIGS. 7 and 10-12. In one embodiment, the stents 30, 70 may include alternating layers of ceramic material and polymeric material as illustrated in FIG. 7. In another embodiment, the stents 30, 70 may include alternating layers of polymeric material having a high concentration of ceramic material and a low concentration of ceramic material. The high concentration layers may comprise ceramic material embedded or dispersed in polymeric material. The low concentration layers may be substantially free or completely free of ceramic material. It should also be appreciated that one layer of polymeric material may have a different composition than another layer of polymeric material. Also, the thickness of the layers may be uniform or may vary.

In one embodiment, the stents 30, 70 may include at least two layers of material, or suitably, at least three layers of material. In another embodiment, the stents 30, 70 may include up to no more than twenty one layers of material or up to no more than fifteen layers of material. The layers of material may be coupled together to form a relatively resilient structure. The polymeric material imparts resiliency to the sheet 32 and ribbon 72 of composite material by distributing the load on bending of the stent 30. The resilient properties of the composite material allow the stent 70 to move from the contracted configuration to the expanded configuration as explained above. The thickness of the sheet 32 may be about 10 to 200 microns, desirably about 30 to 150 microns, or suitably 40 to 100 microns.

The composite material used to form the sheet 32 and/or the ribbon 72 may be bioremovable. For example, the sheet 32 and/or the ribbon 72 may include bioremovable polymer and bioremovable ceramic material in the alternating layers. In one embodiment, the outer two layers of the sheet 32 and/or the ribbon 72 may be bioremovable polymer layers that are substantially free or completely free of bioremovable ceramic material. Thus, the bioremovable ceramic material is included in the interior layers of the sheet 32 and/or ribbon 72. In another embodiment, the outer two layers of the sheet 32 and/or the ribbon 72 may include bioremovable ceramic material. In this configuration, the layers of bioremovable polymer may be on the inside of the sheet 32 and/or the ribbon 72. The layers that include bioremovable ceramic material may be about 1 to 20 microns thick or about 2 to 10 microns thick. Each layer of bioremovable polymer may be about 0.1 to 10 microns thick, 0.5 to 8 microns thick, or 1 to 5 microns thick. The bioremovable polymer and bioremovable ceramic material may be any of the materials described in connection with the stent 10. It should also be appreciated that the bioremovable polymer used in any of the layers need not include only a single polymer or copolymer. Rather, the bioremovable polymer may include mixtures of one or more bioremovable polymers and/or copolymers.

In one embodiment, the bioremovable ceramic material may be fully dense. In another embodiment, the bioremovable ceramic material may be porous to allow it to function as a carrier for bioactive agents or to provide the desired bioremoval rate to the stents 30, 70. For example, the bioremovable ceramic material may have pore sizes from 1 nanometer to 0.1 microns. The methods used to prepare the bioremovable ceramic material may be altered to impart the desired amount of porosity as described in greater detail as follows.

In one embodiment, the bioremovable ceramic material may include a plurality of flakes dispersed within or deposited on an underlying layer of bioremovable polymer. In one embodiment, the flakes may be embedded in the bioremovable polymer so that the flakes are approximately parallel to each other and/or to the surface of the layer. Orienting the flakes in this manner enhances the physical properties of the composite material by increasing its stiffness and/or strength. The parallel orientation of the flakes serves to strengthen the layer of bioremovable composite material in a lengthwise direction and widthwise direction. In another embodiment, chopped fibers of ceramic material may also be added to the sheet 32 and/or ribbon 72, either alone or in combination with flakes of ceramic material. In one embodiment, the chopped fibers may be oriented parallel to each other in a lengthwise direction. In this configuration, the chopped fibers increase the stiffness of the layer in a lengthwise direction, but may not provide any increase or may provide a small increase in stiffness in the crosswise direction.

It should be appreciated that the flakes of ceramic material may be any suitable size. It is preferred, however, to use flakes having an aspect ratio of approximately 5 to 50, approximately 7 to 30, or approximately 10 to 20. The aspect ratio is the ratio of the length (i.e., the longest dimension of its flat side) to its thickness. The flakes may also be approximately 1 to 50 microns thick and up to 300 microns or, desirably, 200 microns wide. Accordingly, flakes of ceramic material having an aspect ratio of up to 300 may be suitable for use in some bioremovable polymers. Thus flakes with the aspect ratio range of 5 to 300 may be used in certain embodiments.

The flakes may be prepared using any suitable process. In one embodiment, the flakes are prepared using the sol method described above except that instead of forming fibers, the sol, for example of tricalcium phosphate, is cast as a solution onto a plate where after drying it is broken into small pieces and screened to get uniform sized flakes. The flakes are then sintered at various temperatures to finish the process and impart the desired porosity to the flakes. The flakes may be fired at about 1100 to 1200° C. to achieve full density or at 750 to 850° C. to provide nano-porous flakes, i.e., flakes that have a mean pore size of approximately 1 nanometer to 0.1 nanometer. The flakes may be fired in a drop furnace to prevent the flakes from sticking together. Openings may be cut in the sheet 32 and/or ribbon 72 as shown in FIGS. 8-9 and 13-14.

In another embodiment, very thin flakes of ceramic material (1 to 10 microns thick) can be made by preparing a very dilute solution of the ceramic material. A very thin coating of this solution is made on an alumina plate or setter after which it is dried at approximately 60 to 70° C. The flakes are then held at this temperature before being loaded into a furnace that is heated to the desired sintering temperature as discussed above. After sintering, the flakes are removed from the alumina setter. The aspect ratio range of these flakes is on the order of 10 to 50. It should be appreciated that this method may be modified to use flash drying techniques to allow for timely production of larger quantities of flakes.

The flakes may also be made using a water dispersion of nano particles of ceramic material (e.g., amorphous calcium phosphate). This dispersion is coated onto an alumina setter plate using a Mayer rod. The coating is then dried and sintered at the desired temperature as described above. The thickness of flakes made by this method is somewhat greater than flakes made by the solution method—on the order of 10 to 30 microns thick. The aspect ratio of these flakes was approximately 5 to 20. Both this technique and the solution technique when applied to amorphous calcium phosphate produced flakes of tricalcium phosphate. It should be appreciated that larger scale production methods may be obtained by coating the water dispersion or the solution onto suitable polymer films. The flakes may be removed by bending or stretching the film to crack and pop the flakes off.

Referring to FIG. 7, one embodiment of the sheet 32 is shown having five layers of material. More specifically, the sheet 32 includes a top layer of bioremovable polymer material 44, an intermediate layer of bioremovable polymer material 46, and a bottom layer of bioremovable polymer material 48. In between the top layer 44 and the intermediate layer 46 is a first layer of bioremovable ceramic material 50, and in between the intermediate layer 46 and the bottom layer 48 is a second layer of bioremovable ceramic material 52. It should be appreciated that the sheet 32 may have more or less than five layers. For example, the sheet 32 may have at least three layers, at least five layers, at least seven layers, or at least nine layers. Also, it should be appreciated that the ribbon 70 may also be configured to have a similar layer structure as that shown for the sheet 32.

Figure 8:
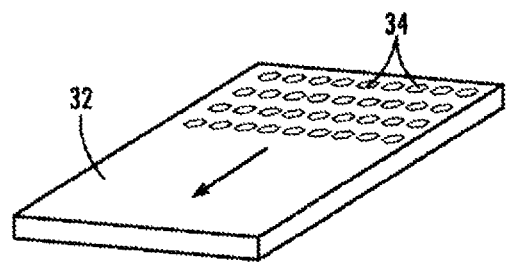
FIG. 8 shows a perspective view of the layered composite material of FIG. 7 as holes are being made in the layered composite material.
Figure 9:
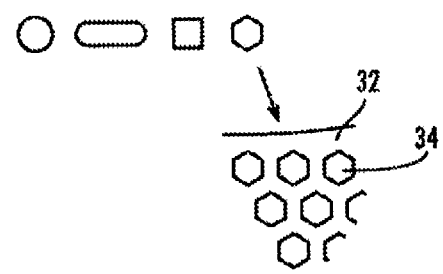
FIG. 9 shows one of a number of embodiments of the geometrical shapes that the holes in the layered composite material of FIG. 8 may have.

Referring to FIGS. 8 and 9, the sheet 32 may include openings 34 having any of a number of suitable shapes. For example, as shown in FIG. 9, the openings 34 may include hexagonal openings, or, in other embodiments, square, circular, oval, or other shaped openings. The openings 34 may be provided to allow the lumen tissue to still be in contact with the material moving through the lumen.

The sheet 32 may be a continuous sheet of, for example, sintered tricalcium phosphate on the order of 10 microns thick. The sheet 32 may be made using the process described in U.S. Pat. Nos. 3,436,307 and 3,444,929, both of which are hereby incorporated by reference herein in their entireties. In this process, a dispersion of submicron to micron size particles of ceramic material is dispersed with a binder in a liquid, e.g., about 10% methylcellulose in water or alternatively polyvinyl butyral in toluene or other suitable solvent. The dispersion is tape-cast onto a plastic sheet and dried. The sheet may then be sintered to keep it flat. Such sheets can have a thickness of about 10 to 20 microns. Sintering to achieve flat sheets may require placing alumina microspheres under and over the sheets. The particles of tricalcium phosphate in this example are expected to meet ASTM purity standards F1088-04a for use as implants. The stent sheets are then used to construct an alternating layer structure, bioremovable polymer/ceramic as described above for the flake construction. It should be appreciated that this method may also be used to make flakes of ceramic material if the sheet is broken into appropriately sized flakes (e.g., sheet broken and screened to separate out appropriate sized flakes).

The sheet 32 may be prepared by coating a ceramic material sheet with a solution of 0.1 grams of PLA/PGA copolymer (90/10 to 10/90) in 5 cc of a suitable solvent such as methylene chloride or acetone. Once the ceramic material sheet has been completely coated, another ceramic material sheet is positioned over the coated side of the first ceramic material sheet. The coating process may then be repeated on this new composite ceramic polymer material sheet. This process is used to provide the desired number of layers in the sheet 32. It should also be appreciated that this process may be used to prepare a ribbon shaped composite material having the layer characteristics shown in FIG. 7.

FIGS. 10 and 11 show side and top views, respectively, of one embodiment of a ribbon or layer 80 that is used as one of the layers in the ribbon 72 of composite material. These FIGS. show the flakes 78 oriented parallel to the flat planar side of the ribbon 70 and to each other. FIG. 12 shows one embodiment of the ribbon 72 having five layers of material. Specifically, the ribbon 72 includes a top layer 84 of bioremovable polymer material, an intermediate layer 86 of bioremovable polymer material, and a bottom layer 88 of bioremovable polymer material. In between the top layer 84 and the intermediate layer 86 is a first layer 90 of bioremovable polymer embedded with bioremovable ceramic material, and in between the intermediate layer 86 and the bottom layer 88 is a second layer 92 of bioremovable polymer embedded with bioremovable ceramic material. It should be appreciated that the ribbon 70 may have more or less than five layers. For example, the ribbon may have at least three layers, at least five layers, at least seven layers, or at least nine layers of material. Also, it should be appreciated that the sheet 32 may also be configured to have a similar layer structure as that shown for the ribbon 70.

The ribbon may be prepared using any suitable process. In one embodiment, the different layers of material may be prepared individually and coupled together to form the layered bioremovable composite material. For example the different layers of bioremovable polymer having high and low concentrations of bioremovable ceramic material may be extruded as a viscous polymer or molded individually (e.g., liquid polymer with dispersion of ceramic material is placed in an appropriately sized mold until dry). The individual layers may be coupled together by heating a sandwich of layers or slightly solvating the surface of each layer before applying the next layer. In the extrusion process, the high concentration layers may be made by extruding a mixture of bioremovable polymer and bioremovable ceramic material into a ribbon or strip of bioremovable composite material. The low concentration layers may be made by extruding bioremovable polymer into a ribbon. In the cast and mold process, ribbons of bioremovable polymer and ribbons of a combination of bioremovable polymer and bioremovable ceramic material may be made by casting the liquid bioremovable polymer and the mixture of bioremovable polymer and bioremovable ceramic material into molds. Once the ribbons have dried, the ribbons may be removed from the mold and coupled together to form a layered bioremovable composite material. The bioremovable composite material made using either process can then be used to make the finished composite stent.

In another embodiment, the bioremovable composite material may be prepared by extruding a mixture of bioremovable polymer and bioremovable ceramic material in the shape of a tube. The tube may be cut to have a resilient helical shape. The bioremovable composite material may also be prepared using an integrated process where the different layers of material are simultaneously extruded and immediately coupled together.

One or more bioactive agents (also referred to herein as therapeutic agents) may be coated onto the stents 10, 30 or embedded inside the stents 10, 30. For example, bioactive agents may be embedded in the bioremovable polymer so that as the stents 10, 30 degrade, the bioactive agent is slowly released. In another embodiment, the bioremovable ceramic material may be porous and impregnated with the bioactive agent. As the bioremovable ceramic material is exposed and removed, the bioactive agents may be released. The concentration of bioactive agents in the stents 10, 30 may be selected based on the rate at which the stents 10, 30 are removed so that the appropriate dose of bioactive agent is continually being released until the stents 10, 30 have fully degraded.

It should be appreciated that any one or combination of a wide variety of bioactive agents may be suitable to be used with the stents 10, 30 depending on the application and the particular pathology. The term "bioactive agent" includes pharmacologically active substances that produce a local or systemic effect in a patient. The term thus means any pharmacological substance intended for use in the diagnosis, cure, mitigation, treatment or prevention of disease or in the enhancement of desirable physical or mental development and conditions in a patient. Bioactive agents that may be used in connection with a vascular stent include drugs such as heparin, prostacyclin, angiopeptin, and/or methotrexate. Other bioactive agents that may be used include, without limitation: antiinfectives such as antibiotics and antiviral agents; chemotherapeutic agents (i.e. anticancer agents); anti-rejection agents; analgesics and analgesic combinations; anti-inflammatory agents; hormones such as steroids; growth factors such as vascular endothelial growth factor (VEGF); stem cells, and other naturally derived or genetically engineered proteins, polysaccharides, glycoproteins, or lipoproteins. In one embodiment, the stent may be coated with stem cells to facilitate tissue repair at the site of the occlusion in the lumen. The outside surface of the stent may also be coated with ceramic material (e.g., flakes of bioremovable ceramic material) to provide a suitable surface structure for the stem cells to grow on.

EXAMPLES

The following examples are provided to further illustrate the subject matter disclosed herein. The following examples should not be considered as being limiting in any way.

Example 1

Preparation of Layered Polymer/Ceramic Composite

In this example, a multi-layer composite ribbon was prepared using high aspect ratio thin flakes as follows. It should be appreciated that although the ceramic material is not bioremovable, this example demonstrates the feasibility of making the polymer ceramic composite material. Other bioremovable ceramic materials may be substituted for the titania.

Two polymer solutions were initially prepared. The first solution ("Solution A") contained 20 wt. % of bioremovable polymer (50/50 PLA/PGA copolymer available from Lakeshore Biomaterials as 5050DL High IV) in acetone. The second solution ("Solution B") was the same as Solution A with titania flakes added (approximately ⅓ of the volume was titania flakes). The titania flakes were prepared using the sol-gel process described in U.S. Pat. No. 3,709,706 issued to Sowman, which is hereby incorporated by reference in its entirety.

The solutions were used to prepare a seven layer ribbon by applying alternating coats of each solution on top of each other starting with Solution A. Each layer was allowed to dry before the next layer was added. When each coating was applied to the dried layer, the solvent/polymer material from the coating acted to slightly solvate the very top of the dried layer thereby adhering the layers together. Each coating of Solution B was thin enough that the flat surfaces of the flakes in the coating were oriented parallel to the flat surface of the ribbon.

Example 2

Preparation of Calcium Phosphate Flakes from Solution

In this example, tricalcium phosphate flakes were prepared from solution as follows. A solution was formed by adding 2 grams of amorphous calcium phosphate powder (available from Plasma-Biotal, Ltd. as Captal A.C.P.) to 80 ml of an 11.1 wt. % solution of citric acid (Aldrich) in water. The mixture was stirred for one hour at room temperature to form a slightly cloudy liquid. The slightly cloudy liquid was passed through a 0.2 micron syringe filter to remove undissolved debris, resulting in a clear solution. Several flat alumina plates were coated with this solution by spreading the solution over the surface with a glass rod. The plates were placed in an oven that was heated at 65° C. until the coating dried. The dried coating was clear in appearance. Once the coating had dried, the plates were transferred from the oven to a furnace where the coating was sintered at 650° C. in air. The sintered coating was white in appearance. The thin white coating was scraped off the alumina plates with a razor blade to produce flakes.

Example 3

Preparation of Calcium Phosphate Flakes from Dispersion

In this example, tricalcium phosphate flakes were prepared from an aqueous dispersion as follows. A flat smooth alumina plate was cleaned with acetone and coated with an aqueous dispersion of amorphous calcium phosphate nanoparticles (available from Plasma-Biotal as Tri Calcium Orthophosphate $Ca_3PO_4$ water suspension) using a #20 Mayer rod. The plate was placed in an oven heated at 65° C. until the coating dried. Once the coating had dried, the plate was transferred to a kiln and fired at 1150° C. in air. The resulting ceramic flakes were thin and strong.

Example 4

Preparation of a Helical Ribbon of Composite Material Using PCL

In this example, a helical shaped composite material was prepared as follows. Initially two solutions were prepared. The first solution ("Solution C") was prepared by adding PCL (available from Solvay as CAPA 6500) to methylene chloride to form a 7.7 wt. % solution of PCL. The second solution ("Solution D") was formed by adding 1.0 wt. % tricalcium phosphate flakes prepared in Example 3 to Solution C. Solutions C and D were loaded into separate rectangular templates (each template was approximately 6.4 mm wide, 200 mm long, and 0.44 mm deep) to dry at room temperature in air. Once the ribbons dried, the ribbons were cut from the templates. This method was used to make three strips from Solution C and two ribbons from Solution D.

The dried ribbons were stacked on top of each other in alternating fashion with the ribbons of Solution D positioned between the ribbons of Solution C. The stack was then clamped between two flat metal plates and placed in an oven heated at 60° C. overnight to adhere the layers together. Once the layers were adhered together, the composite material was coiled around a glass rod. Tape and a wire mesh sleeve were used to hold the composite material in place. This assembly was heated overnight at 60° C. to set the helical shape. The result was a helical ribbon of composite material that had an internal diameter that was approximately the same size as the diameter of the glass rod.

Example 5

Preparation of a Helical Ribbon of Composite Material Using PLA/PGA

In this example, the method from Example 4 was repeated except that a solution of PLA/PGA polymer (50/50 PLA/PGA available from Lakeshore Biomaterials as 5050DL High IV) was substituted for the PCL. The composite material stack was not heated since the individual ribbons of material adhered strongly to each other in air at room temperature. The composite material was coiled around the glass rod and left overnight at room temperature to create the coil shape. The result was a helical ribbon of composite material that had an internal diameter that was approximately the same size as the diameter of the glass rod.

Example 6

Preparation of a Narrow Helical Ribbon of Composite Material

In this example, a stack of alternating ribbons of material was made as described in Example 4. After the stack was heat pressed to seal the layers together, approximately 1.6 mm of material was trimmed from each long edge. The composite material was coiled and heated as previously described to produce a smaller, finer helical structure.

Example 7

Preparation of Bioremovable Polymer Material Using PLA/PGA/PCL

In this example, a bioremovable polymer was prepared using PLA/PGA/PCL. A flexible ribbon of polymer material was prepared by coating a 15.9 wt. % solution of PLA/PGA/PCL copolymer (38/12/50 PLA/PGA/PCL, available from Lakeshore Biomaterials as 381250 DLGCL 2E) in methylene chloride (Aldrich) onto a glass sheet and allowing it to dry at room temperature. The resulting flexible ribbon of polymer material was easily peeled from the glass surface.

Illustrative Embodiments

Reference is made in the following to a number of illustrative embodiments of the subject matter described herein. The following embodiments illustrate only a few selected embodiments that may include the various features, characteristics, and advantages of the subject matter as presently described. Accordingly, the following embodiments should not be considered as being comprehensive of all of the possible embodiments. Also, features and characteristics of one embodiment may and should be interpreted to equally apply to other embodiments or be used in combination with any number of other features from the various embodiments to provide further additional embodiments, which may describe subject matter having a scope that varies (e.g., broader, etc.)

from the particular embodiments explained below. Accordingly, any combination of any of the subject matter described herein is contemplated.

According to one embodiment, a composite stent comprises: a loose network of woven fibrous material configured to expand in a lumen, the fibrous material including bioremovable ceramic material; and a bioremovable polymer which coats the fibrous material. The bioremovable ceramic material may include calcium phosphate material and/or bioactive glass. The bioremovable ceramic material may include tricalcium phosphate. The bioremovable polymer may be a first bioremovable polymer and wherein the bioremovable ceramic material may be coated with the first bioremovable polymer and the first bioremovable polymer may be coated with a second bioremovable polymer. The second bioremovable polymer may have a modulus of elasticity that is lower than the first bioremovable polymer. The bioremovable polymer may have elastomeric properties such that the fibrous materials resist sliding past one another when the stent is expanded.

According to another embodiment, a composite stent comprises: a plurality of composite yarns woven together to form a network configured to expand in a lumen, each of the plurality of composite yarns including a plurality of bioremovable ceramic fibers coated with a bioremovable polymer; wherein at least substantially all of the plurality of bioremovable ceramic fibers are positioned substantially parallel to each other. The bioremovable polymer may be a first bioremovable polymer and wherein the composite stent comprises a second bioremovable polymer which forms a coating over the first bioremovable polymer. The first bioremovable polymer may provide resiliency to the composite stent and the first bioremovable polymer and/or the second bioremovable polymer may provide sufficient friction to hold the network in place upon expansion in the lumen. The first bioremovable polymer may comprise polylactide and/or polyglycolide. The bioremovable ceramic fibers may include tricalcium phosphate.

According to another embodiment, a composite stent comprises: a continuous cylindrical network of woven fibrous material configured to expand in a lumen, the fibrous material including bioremovable ceramic material; and a bioremovable polymer which coats the fibrous material.

According to another embodiment, a composite stent comprises: a network of woven fibrous material configured to expand in a lumen without substantial rotational movement of the fibrous material relative to a longitudinal axis of the composite stent, the fibrous material including bioremovable ceramic material; and a bioremovable polymer which coats the fibrous material.

According to another embodiment, a composite stent comprises: a plurality of substantially cylindrical composite yarns woven together to form a network which is configured to expand in a lumen, each of the plurality of composite yarns including a plurality of bioremovable ceramic fibers coated with a bioremovable polymer.

According to another embodiment, a composite stent comprises: a plurality of composite yarns which form a loose, woven, continuous, cylindrical network configured to expand in a lumen, each of the plurality of composite yarns including a plurality of bioremovable ceramic fibers oriented substantially parallel to each other; wherein the plurality of bioremovable ceramic fibers are coated with a first bioremovable polymer and the first bioremovable polymer is coated with a second bioremovable polymer.

According to another embodiment, a composite stent comprises: a first layer comprising bioremovable ceramic material; a second layer comprising a bioremovable polymer, the second layer being coupled to the first layer to form a sheet; wherein the sheet is coiled and configured to expand in a lumen. The bioremovable ceramic material may include calcium phosphate material and/or bioactive glass. The bioremovable ceramic material may include tricalcium phosphate. The bioremovable polymer may comprise polylactide and/or polyglycolide. The composite stent may comprise a third layer which includes bioremovable polymer, the third layer being coupled to the first layer so that the first layer is positioned between the first layer and the third layer. The composite stent may comprise a fourth layer which includes a bioremovable ceramic material and a fifth layer which includes bioremovable polymer, the fourth layer being coupled to the third layer and the fifth layer being coupled to the fourth layer so that the fourth layer is positioned between the third layer and the fifth layer. The sheet may include a plurality of openings. The openings may have any suitable geometrical shape such as hexagonal, circular, triangular, and the like. The sheet may be about 10 microns to 200 microns thick. The first layer may include a plurality of flakes of bioremovable ceramic material.

According to another embodiment, a composite stent comprises: a first layer comprising bioremovable ceramic flakes; a second layer comprising a bioremovable polymer, the second layer being coupled to the first layer to form a sheet; wherein the sheet is wound and configured to expand in a lumen.

According to another embodiment, a composite stent comprises: a plurality of layers comprising a layer which includes a bioremovable ceramic material which is coupled to another layer which includes a bioremovable polymer; wherein the plurality of layers is wound and configured to expand in a lumen.

According to another embodiment, a composite stent comprises: a multi layer sandwich which includes a layer of bioremovable ceramic material coupled to a layer which includes a bioremovable polymer which provides resilience to the sandwich; wherein the sandwich includes plurality of holes therethrough; wherein the sandwich is configured to be wound and inserted into a lumen; and wherein the sandwich is configured to unwind and expand to a fixed position in the lumen. The layer of ceramic material may include bioremovable ceramic material.

According to another embodiment, a composite stent comprises: a plurality of layers that include bioremovable polymer; and a plurality of flakes of bioremovable ceramic material; wherein the plurality of layers alternate between having a high concentration of the plurality of flakes and having a low concentration of the plurality of flakes; and wherein the composite stent is expandable. The bioremovable ceramic material may include tricalcium phosphate. The bioremovable polymer may include polylactide, polyglycolide, polycaprolactone, and/or copolymers thereof. The layers that have a low concentration of bioremovable ceramic material may be substantially free or completely free of any of the plurality of flakes. The plurality of layers may include at least three layers that have a low concentration of the plurality of flakes. The composite stent may be resilient and the resilient properties of the composite stent may cause it to move from a contracted configuration where the composite stent is sized to be positioned in a bodily lumen to an expanded configuration where the composite stent is sized to hold the bodily lumen open. Each of the plurality of flakes may be porous. The composite stent may comprise a bioactive agent positioned in the pores of the plurality of flakes. The bioactive agent may includes heparin, prostacyclin, angiopeptin, and/or methotrexate.

According to another embodiment, a composite stent comprises: a layer of bioremovable polymer that includes a plurality of flakes of bioremovable ceramic material dispersed in the bioremovable polymer; wherein the plurality of flakes of bioremovable ceramic material are oriented parallel to each other and to the surfaces of the layer. The bioremovable ceramic material may include tricalcium phosphate. The bioremovable polymer may include polylactide, polyglycolide, polycaprolactone, and/or copolymers thereof. The average aspect ratio of the plurality of flakes may be approximately 10 to 20. Each of the plurality of flakes may be porous. The layer may be a first layer and wherein the composite stent includes a second layer of bioremovable polymer coupled to the first layer, the second layer being substantially free or completely free of any bioremovable ceramic material.

According to another embodiment, a composite stent comprises a plurality of flakes of bioremovable ceramic material embedded in bioremovable polymer. The bioremovable ceramic material may include tricalcium phosphate. The bioremovable polymer may include polylactide, polyglycolide, polycaprolactone, and/or copolymers thereof. The composite stent may be coated with stem cells. The average aspect ratio of the plurality of flakes may be approximately 5 to 30. The average aspect ratio of the plurality of flakes may be approximately 10 to 20. The composite stent may comprise a first layer that includes the plurality of flakes and a second layer of bioremovable polymer coupled to the first layer, the second layer being substantially free or completely free of any bioremovable ceramic material. Each of the plurality of flakes may be porous. The composite stent may comprise a bioactive agent positioned in the pores of the plurality of flakes. The bioactive agent may include heparin, prostacyclin, angiopeptin, and/or methotrexate.

According to another embodiment, a composite stent comprises: bioremovable polymer; and bioremovable ceramic material; wherein the composite stent has a helical shape; and wherein the composite stent is resilient and resilient properties of the stent cause it to move from a contracted configuration to an expanded configuration. The composite stent may be wound and in a state of tension in the contracted configuration and the composite stent is at least substantially unwound and not in a state of tension in the expanded configuration. The composite stent may have a plurality of openings in it. The composite stent may comprise a first layer that includes the bioremovable ceramic material embedded in the bioremovable polymer and a second layer of bioremovable polymer coupled to the first layer, the second layer being substantially free or completely free of any bioremovable ceramic material.

According to another embodiment, a composite stent comprises: a ribbon of bioremovable polymer; and a plurality of flakes of bioremovable ceramic material embedded in the bioremovable polymer; and a plurality of chopped fibers of bioremovable ceramic material embedded in the bioremovable polymer; wherein the flakes are parallel to a surface of the ribbon and the fibers are parallel to a longitudinal direction of the ribbon. The composite stent may be expandable. The mean length of the plurality of fibers may be approximately 50 to 200 microns and the mean diameter of the plurality of fibers may be approximately 5 to 20 microns. The composite stent may have a plurality of openings in it. The composite stent may be resilient and the resilient properties of the composite stent may cause it to move from a contracted configuration where the composite stent is sized to be inserted into a lumen to an expanded configuration where the composite stent supports and/or dilates the lumen. The composite stent may comprise a plurality of layers of bioremovable polymer that alternate between having a high concentration of the plurality of flakes and/or the plurality of fibers and having a low concentration of the plurality of flakes and/or the plurality of fibers.

According to another embodiment, a method of making bioremovable composite material comprises: extruding a mixture of bioremovable polymer and bioremovable ceramic material to form the bioremovable composite material. The bioremovable composite material may include a plurality of flakes of bioremovable ceramic material. The method may comprise heating the mixture as the mixture is extruded. The method may comprise making openings in the bioremovable composite material. The bioremovable composite material may have alternating layers that have a high concentration of bioremovable ceramic material and a low concentration of bioremovable ceramic material. The method may comprise coupling the bioremovable composite material to bioremovable polymer. The method may comprise using the bioremovable composite material to make a composite stent that is configured to move from a contracted configuration where the composite stent is sized to be positioned in a bodily lumen to an expanded configuration where the composite stent is sized to hold the bodily lumen open.

According to another embodiment, a method of making bioremovable composite material comprises: coupling a first layer of bioremovable polymer that is substantially free or completely free of bioremovable ceramic material to a second layer of bioremovable polymer that includes bioremovable ceramic material embedded therein. The method may comprise coupling the second layer to a third layer of bioremovable polymer that is substantially free or completely free of bioremovable ceramic material and coupling the third layer to a fourth layer of bioremovable polymer that includes bioremovable ceramic material embedded therein. The method may comprise heating the first layer and the second layer to couple the first layer and the second layer together. The method may comprise solvating a surface of the first layer and coupling the second layer to the solvated surface of the first layer. The bioremovable ceramic material embedded in the second layer may include a plurality of flakes of bioremovable ceramic material.

According to another embodiment, a method of making bioremovable composite material comprises: mixing bioremovable ceramic material with bioremovable polymer to form a first mixture; solidifying the first mixture in a mold to form a first ribbon; coupling the first ribbon and a second ribbon together to form a bioremovable composite material, the second ribbon including bioremovable polymer. A plurality of flakes of bioremovable ceramic material may be mixed with the bioremovable polymer to form the first mixture. The bioremovable ceramic material may be mixed with the bioremovable polymer to form the first mixture includes tricalcium phosphate. The method may comprise solidifying bioremovable polymer in a mold to form the second ribbon. The method may comprise heating the first ribbon and the second ribbon to couple the first ribbon and the second ribbon together. The method may comprise coiling the bioremovable composite material to form a composite stent. The second ribbon may be substantially free or completely free of bioremovable ceramic material.

According to another embodiment, a method of using a composite stent comprises: positioning the composite stent in a bodily lumen, the composite stent including bioremovable polymer and bioremovable ceramic material, the composite stent being in a contracted configuration where the composite stent is coiled in a state of tension; and releasing the composite stent so that the resilient properties of the composite stent cause the composite stent to expand in the bodily lumen.

The terms recited in the claims should be given their ordinary and customary meaning as determined by reference to relevant entries (e.g., definition of "plane" as a carpenter's tool would not be relevant to the use of the term "plane" when used to refer to an airplane, etc.) in dictionaries (e.g., consensus definitions from widely used general reference dictionaries and/or relevant technical dictionaries), commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used herein in a manner more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure [the term] shall mean," etc.). References to specific examples, use of "i.e.," use of the word "invention," etc., are not meant to invoke exception (b) or otherwise restrict the scope of the recited claim terms. Accordingly, the subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be read to be given their broadest interpretation in view of the prior art and the ordinary meaning of the claim terms.

As used herein, spatial or directional terms, such as "left," "right," "front," "back," and the like, relate to the subject matter as it is shown in the drawing FIGS. However, it is to be understood that the subject matter described herein may assume various alternative orientations and, accordingly, such terms are not to be considered as limiting. Furthermore, as used herein (i.e., in the claims and the specification), articles such as "the," "a," and "an" can connote the singular or plural. Also, as used herein, the word "or" when used without a preceding "either" (or other similar language indicating that "or" is unequivocally meant to be exclusive e.g., only one of x or y, etc.) shall be interpreted to be inclusive (e.g., "x or y" means one or both x or y). Likewise, as used herein, the term "and/or" shall also be interpreted to be inclusive (e.g., "x and/or y" means one or both x or y). In situations where "and/or" or "or" are used as a conjunction for a group of three or more items, the group should be interpreted to include one item alone, all of the items together, or any combination or number of the items. Moreover, terms used in the specification and claims such as have, having, include, and including should be construed to be synonymous with the terms comprise and comprising.

Unless otherwise indicated, all numbers or expressions, such as those expressing dimensions, physical characteristics, etc. used in the specification are understood as modified in all instances by the term "about." At the very least, and not as an attempt to limit the application of the doctrine of equivalents to the claims, each numerical parameter recited in the specification or claims which is modified by the term "about" should at least be construed in light of the number of recited significant digits and by applying ordinary rounding techniques. Moreover, all ranges disclosed herein are to be understood to encompass any and all subranges subsumed therein. For example, a stated range of 1 to 10 should be considered to include any and all subranges between and inclusive of the minimum value of 1 and the maximum value of 10; that is, all subranges beginning with a minimum value of 1 or more and ending with a maximum value of 10 or less (e.g., 5.5 to 10).

What is claimed is:

1. A composite stent comprising:
a plurality of layers that include bioremovable polymer; and
a plurality of flakes of bioremovable ceramic material, the flakes having a length and a thickness defining an aspect ratio;
wherein the plurality of layers alternate between having a high concentration of the plurality of flakes and having a low concentration of the plurality of flakes; and
wherein the composite stent is expandable.

2. The composite stent of claim 1 wherein the bioremovable ceramic material includes tricalcium phosphate.

3. The composite stent of claim 1 wherein the bioremovable polymer includes polylactide, polyglycolide, polycaprolactone, and/or copolymers thereof.

4. The composite stent of claim 1 wherein each of the plurality of flakes is porous.

5. The composite stent of claim 4 comprising a bioactive agent positioned in the pores of the plurality of flakes.

6. The composite stent of claim 1 wherein the aspect ratio of the plurality of flakes is 5 to 300.

7. The composite stent of claim 1 wherein the plurality of flakes provide strength, stiffness, or a combination thereof to the composite stent in the direction of both the width and length of the layers possessing flakes.

8. A composite stent comprising:
bioremovable polymer; and
a plurality of flakes of bioremovable ceramic material included in the bioremovable polymer, the flakes having a length and a thickness defining an aspect ratio;
wherein the composite stent has a helical shape; and
wherein the composite stent is resilient and resilient properties of the stent cause it to move from a contracted configuration to an expanded configuration.

9. The composite stent of claim 8 wherein the composite stent is wound and in a state of tension in the contracted configuration and the composite stent is at least substantially unwound and not in a state of tension in the expanded configuration.

10. The composite stent of claim 8 wherein the composite stent has a plurality of openings in it.

11. The composite stent of claim 8 comprising a first layer that includes the plurality of flakes of bioremovable ceramic material embedded in the bioremovable polymer and a second layer of bioremovable polymer coupled to the first layer, the second layer having a plurality of flakes of bioremovable ceramic material embedded in the bioremovable polymer, the second layer having a concentration of flakes of bioremovable ceramic powder different than the first.

12. The composite stent of claim 8 wherein the aspect ratio of the plurality of flakes is 5 to 300.

13. A composite stent comprising a plurality of flakes of bioremovable ceramic material embedded in bioremovable polymer, the flakes having a length and a thickness defining an aspect ratio and wherein the bioremovable polymer forms a bioremovable stent.

14. The composite stent of claim 13 wherein the bioremovable ceramic material includes tricalcium phosphate.

15. The composite stent of claim 13 wherein the composite stent is coated with stem cells.

16. The composite stent of claim 13 wherein the aspect ratio of the plurality of flakes is 5 to 300.

17. The composite stent of claim 13 wherein the aspect ratio of the plurality of flakes is 10 to 20.

18. The composite stent of claim 13 comprising a first layer that includes the plurality of flakes and a second layer of bioremovable polymer coupled to the first layer, the second layer being substantially free or completely free of any bioremovable ceramic material.

19. The composite stent of claim 13 wherein each of the plurality of flakes is porous.

20. The composite stent of claim 19 comprising a bioactive agent positioned in the pores of the plurality of flakes.

21. The composite stent of claim 20 wherein the bioactive agent includes heparin, prostacyclin, angiopeptin, and/or methotrexate.

22. The composite stent of claim 13 wherein the flakes of bioremovable ceramic material are oriented in parallel.

23. A method of using a composite stent comprising:
positioning the composite stent in a bodily lumen, the composite stent including bioremovable polymer and a plurality of flakes of bioremovable ceramic material, the flakes having a length and a thickness defining an aspect ratio, the composite stent being in a contracted configuration where the composite stent is coiled in a state of tension; and
releasing the composite stent so that the resilient properties of the composite stent cause the composite stent to expand in the bodily lumen.

* * * * *